United States Patent [19]

Goeddel et al.

[11] Patent Number: 5,231,176
[45] Date of Patent: Jul. 27, 1993

[54] DISTINCT FAMILY DNA ENCODING OF HUMAN LEUKOCYTE INTERFERONS

[75] Inventors: David V. Goeddel, Hillsborough; Harold M. Shepard, San Francisco, both of Calif.

[73] Assignee: Genentech, Inc., South San Francisco, Calif.

[21] Appl. No.: 895,902

[22] Filed: Jun. 9, 1992

Related U.S. Application Data

[60] Division of Ser. No. 520,976, May 11, 1990, Pat. No. 5,120,832, which is a continuation of Ser. No. 644,740, Aug. 27, 1984, abandoned.

[51] Int. Cl.[5] ............... C07H 15/12; C12P 21/06; C12N 1/22
[52] U.S. Cl. ............... 435/69.51; 435/252.3; 435/320.1; 530/351; 424/85.7; 424/85.4; 536/23.52
[58] Field of Search ............ 536/27; 435/69.51, 252.3, 435/320.1; 530/351; 424/85.7, 85.4

[56] References Cited

FOREIGN PATENT DOCUMENTS 0032134 10/1981 European Pat. Off. .
0048970 4/1982 European Pat. Off. .
0170204 7/1985 European Pat. Off. .
8302460 7/1983 PCT Int'l Appl. .
8400776 3/1984 PCT Int'l Appl. .

OTHER PUBLICATIONS

Lawn et al. *PNAS* 78(9): 5435–5439 (1981).
Goeddel et al. *NAR* 8(18):4057–4074 (1980).
Goeddel, et al., *Nature* 287, 411 (1980).
Capon, et al., *Mol. and Cell Biol.*, 5 768 (1985).
Goeddel, et al., *nature* 290 20 (1981).

*Primary Examiner*—Robert J. Hill, Jr.
*Assistant Examiner*—Shelly J. Guest
*Attorney, Agent, or Firm*—Walter H. Dreger

[57] ABSTRACT

This invention related to the discovery and production by recombinant DNA technology of a novel, distinct family of human leukocyte interferons, having a total amino acid residue number greater than 166 preferably about 172.

7 Claims, 9 Drawing Sheets

DISTINCT FAMILY DNA ENCODING OF HUMAN LEUKOCYTE INTERFERONS

This is a division of application Ser. No. 07/520,976 filed May 11, 1990, now U.S. Pat. No. 5,120,832, a continuation of application Ser. No. 06/644,740, filed Aug. 27, 1984, now abandoned.

FIELD OF THE INVENTION

The present invention relates to a novel, distinct family of human leukocyte interferon proteins (designated herein by HuIFN-αII or HuIFN-$\alpha_{II}$ and to species thereof as HuIFN-αII.1 or HuIFN-$\alpha_{II}$1, and so forth) which are useful in the treatment of viral and neoplastic diseases, and to the means for producing such interferon proteins. In general, the present invention finds its basis in the field of recombinant DNA technology which has been employed to discover and produce this novel, distinct family of human leukocyte interferons.

The publications and other materials hereof used to illuminate the background of the invention, and in particular cases, to provide additional details respecting its practice are hereby incorporated by reference, and for convenience are numerically referenced by the following text and respectively grouped in the appended bibliography.

BACKGROUND OF THE INVENTION

A human leukocyte interferon was first discovered and prepared in the form of very crude precipitates from natural source (1). Following this work was the substantial discovery that human leukocyte interferons exist as a class or family of proteins all exhibiting close homology and varying degrees of similar in kind antiviral activity. This work has been documented in several references as follows: (2, 3, 4, 5). This family of leukocyte interferons (commonly referred to in abbreviated form as HuIFN-α) has been reported to be composed of upwards of 15 or more individual species, having varying degrees of similar in kind antiviral activity. Characteristically, these human leukocyte interferon species have been identified by amino acid sequences consisting of from about 165 to 166 amino acids in their mature forms, by the underlying DNA sequence for each and by identification of glycosolation sites and reported antiviral activity in animal species. Indeed, at least one of these human leukocyte interferon proteins is enjoying success in certified human clinical studies. These interferon species have been and are being produced via recombinant DNA technology, notably employing the workhorse in this field, namely a transfected E. coli microorganism. Thus, these previous discoveries have enabled the production currently of sufficient quantities of human leukocyte interferon species via recombinant DNA technology from a transfected host system as to permit the recovery of relatively large amounts of very pure protein finding use for requisite clinical studies. These achievements have been reported in the references cited previously as well as other references forming a part of the state of the art currently.

As a result of the extensive studies that various workers have expended on the study of the human leukocyte interferon family, it was thought beyond doubt that the human leukocyte interferons that have been discovered and studied were composed within a single family of proteins sharing characteristics of homology, amino acid length and antiviral activity. Similar research attended corresponding success for animal, notably bovine, interferons (6).

A second class of human interferons is represented by the so called human fibroblast interferon (β-interferon, or HuIFN-β). Although extensive research into this compound has been conducted, surprisingly it is thought to be a single polypeptide or protein, in contradistinction to the leukocyte series where, as noted above, upwards of 15 or more species are thought to exist within the general definitional term of human leukocyte interferon (7).

A third class of human interferons is represented by human gamma interferon (HuIFN-γ) (8,9). Although human gamma interferon has been reported to exhibit the antiviral and antiproliferative properties characteristic of the human interferons in the leukocyte and fibroblast series, its properties are distinct in that, in contrast to the leukocyte and beta interferons, it is of shorter amino acid length and is pH 2 labile (10). Because of these distinctions, human gamma interferon is thought to be slated more for indications of antiproliferative activity with indications of substantial use in the treatment of cancer patients. Central and independent research has therefore attended the human gamma interferon molecule.

Inasmuch as human fibroblast interferon (HuIFN-β) and human leukocyte interferons (HuIFN-α) are similar structurally (i.e. amino acid length and homologous sequence) and biologically (i.e. antiviral activity), it was thought by many researchers odd that the human leukocyte interferon would be composed of a family of multiple species whereas in the human fibroblast interferon case only one gene has so far been located, indicating evolutionary divergence and expansion to multiple genes within the leukocyte family but retention of a single distinct gene in the case of fibroblast interferon.

Because of this curiosity, the inventors of the present invention chose to search for additional HuIFN-β genes. This effort was manifested by screening at low hybridization stringency a human genomic DNA library (11) utilizing a DNA probe prepared from a fragment spanning the mature coding region of the known HuIFN-β gene. This research resulted in the surprising, serendipitous discovery of a novel, distinct family of human leukocyte interferons not previously known or thought to exist. This discovery of a novel, distinct family of human leukocyte interferons forms the basis of the present invention.

SUMMARY OF THE INVENTION

The present invention relates to the discovery of a novel and distinct family or group within the human leukocyte interferon class of compounds. This new family or group of human leukocyte interferons, although exhibiting substantial homology in its coding region with the previously reported human leukocyte interferon family of genes (e.g.,about 70 percent), are considered distinct from the previously reported family of human leukocyte interferons inasmuch as the homology is not greater than cited above and the length of amino acid residues is greater than than those reported for the earlier class or family of human leukocyte interferons. Thus, the previously reported family of human leukocyte interferons comprise approximately 165 to 166 amino acids in the mature form. The human leukocyte interferons of the present invention, representative of this second family or group of human leukocyte interferons have been found to contain approximately 172 amino acids. Similarly, associated antiviral biological activity indicates that the human leukocyte interferons of the present invention have specifities which overlap but have a broader spectrum of activity compared with those of several of the previously reported human leukocyte interferons.

The present invention relates to and teaches means for producing a new family of human leukocyte interferons which are considered distinct and novel from those human leukocyte interferons previously reported. The present invention enables the production of such novel, distinct human leukocyte interferons via recombinant DNA technology such that they, and each of them, can be prepared in direct, mature form or via fusion protein intermediates, and in amounts sufficient to initiate and conduct clinical testing as prerequisites to marketing approval. The products of this invention are suitable for use, in all of their forms, in the prophylactic or therapeutic treatment of humans, notably for viral infections and malignant and immunosuppressed or immunodeficient conditions. Their forms include various possible oligomeric forms and they may include associated glycosolation as well as allelic variations or other derivatives of individual members or species. The products are produced in accordance with this invention by genetically engineered microorganisms or cell culture systems.

The present invention comprises the novel, distinct family of human leukocyte interferons thus produced and the means and methods for their production. The present invention is further directed to replicable DNA expression vehicles harboring gene sequences encoding the novel, distinct human leukocyte interferons in expressible form. Further, the present invention is directed to microorganism strains or cell cultures transfected with the expression vehicles described above and to fermentation media comprising such transfected strains or cultures, capable of producing the novel, distinct human leukocyte interferons of the present invention.

In still further aspects the present invention is directed to various processes useful for preparing said interferon gene sequences, DNA expression vehicles, microorganism strains and cell cultures and to specific embodiments thereof. Still further, this invention is directed to the preparation of the fermentation media of said microorganisms and cell cultures. Further, in certain host systems, vectors can be devised capable of producing the desired interferons hereof, secreted from the host cell in mature form.

GENERAL DESCRIPTION OF EMBODIMENTS HEREOF

The present invention can be practiced utilizing a variety of bacterial, yeast, or mammalian or vertabrate cell culture systems capable of being successfully transfected with expression vectors harboring the gene sequence of a particular novel, distinct human leukocyte interferon of the present invention. These systems are well known in the art and have been copiously referenced. For example, extensive use of the microorganism E. coli K-12 strain 294 (ATCC No. 31446) finds use in the present invention along with other known E. coli strains known in the art and deposited in various public microorganism depositories. These other microorganisms include for example, strains from Bacillus and Salmonella and Serratia. In addition, various yeast strains have been described and can be employed in the present invention. Most attention has been directed to the strain *Saccharomyces cerevisiae* which has been deposited with the American Type Culture Collection, specifically strain RH218 under ATCC No. 44076. Similarly, various cell culture systems have been developed and used and can be used in the process of the present invention. For example, various cultures such as WI38, BHK, T3, CHO, VERO cell lines can be employed.

For each of these systems, there have been developed and can be employed herein various promoter systems which direct the expression of an operably flanked heterologous gene segment, said heterologous gene segment of the present invention being that encoding a novel, distinct human leukocyte interferon of the present invention. The operable linkage of the gene with a suitable promoter in a given expression host system can be done so as to effect the expression of the novel, distinct human leukocyte interferon of the present invention in so called mature form, that is, devoid of any presequence or other artifact of expression linked to the amino acid sequence. Alternatively, the novel, distinct human leukocyte interferons of the present invention can be operably linked together with its own signal sequence so as to effect secretion of the mature form via use of the cleavage of the signal sequence upon transport through the cell membrane. In addition, the novel, distinct human leukocyte interferon gene of the present invention can be operably linked so as to prepare a fusion protein comprising the amino acid sequence of the novel, distinct human leukocyte interferon hereof together with homologous protein linked to the N-terminus. All of these various embodiments are included within the scope of the present invention, which has for its basic premise the discovery, identification, and enablement of the production of novel, distinct human leukocyte interferons of a class or family not previously reported and having properties and structures which are distinct from those human leukocyte interferons previously reported (see 4).

DESCRIPTION OF A PREFERRED EMBODIMENT

The method of the present invention is illustrated by a particular, representative embodiment by which the novel, distinct leukocyte interferons of the present invention were identified by way of gene sequence, gene isolation, hook-up for expression, purification and biological ascertainment. This method employed the use of the gene for human beta interferon as a probe of the human genomic library, originally intended to determine whether additional beta genes existed. The results of these experiments identified genes which appeared initially not to be beta interferon genes, rather more associated with the leukocyte series of interferons. The work disclosed herein substantiated this conclusion.

DESCRIPTION OF DRAWINGS

FIGS. 2A–2C. DNA sequence relationships between the IFN-αII genes. The sequence of the IFN-αII.1 gene is presented in detail with 250 bases of 5'-flanking sequence (sufficient to encode the region presumably required for viral induction), and 3'-flanking sequence through the putative polyadenylational site. Only those nucleotides of the IFN-αII.2, αII.3 and αII.4 genes which differ from that of IFN-αII.1 are shown. ) (—) Gaps in the IFN-αII.1 sequence which accommodate insertions in the other genes; (Δ—Δ—Δ), deletions in the IFN-αII.2, αII.3 and αII.4 sequences which maximize homology with IFN-αII.1; (*) indicates the putative messenger RNA cap site of IFN-αII.1; (←) the 5'-flanking region; (→) the 3'-flanking region. IFN-αII.4 sequence was not obtained upstream of position 199. The first two nucleotides of IFN-αII.4 are not shown since they are identical to the corresponding bases of IFN-αII.1.

Figure 3:
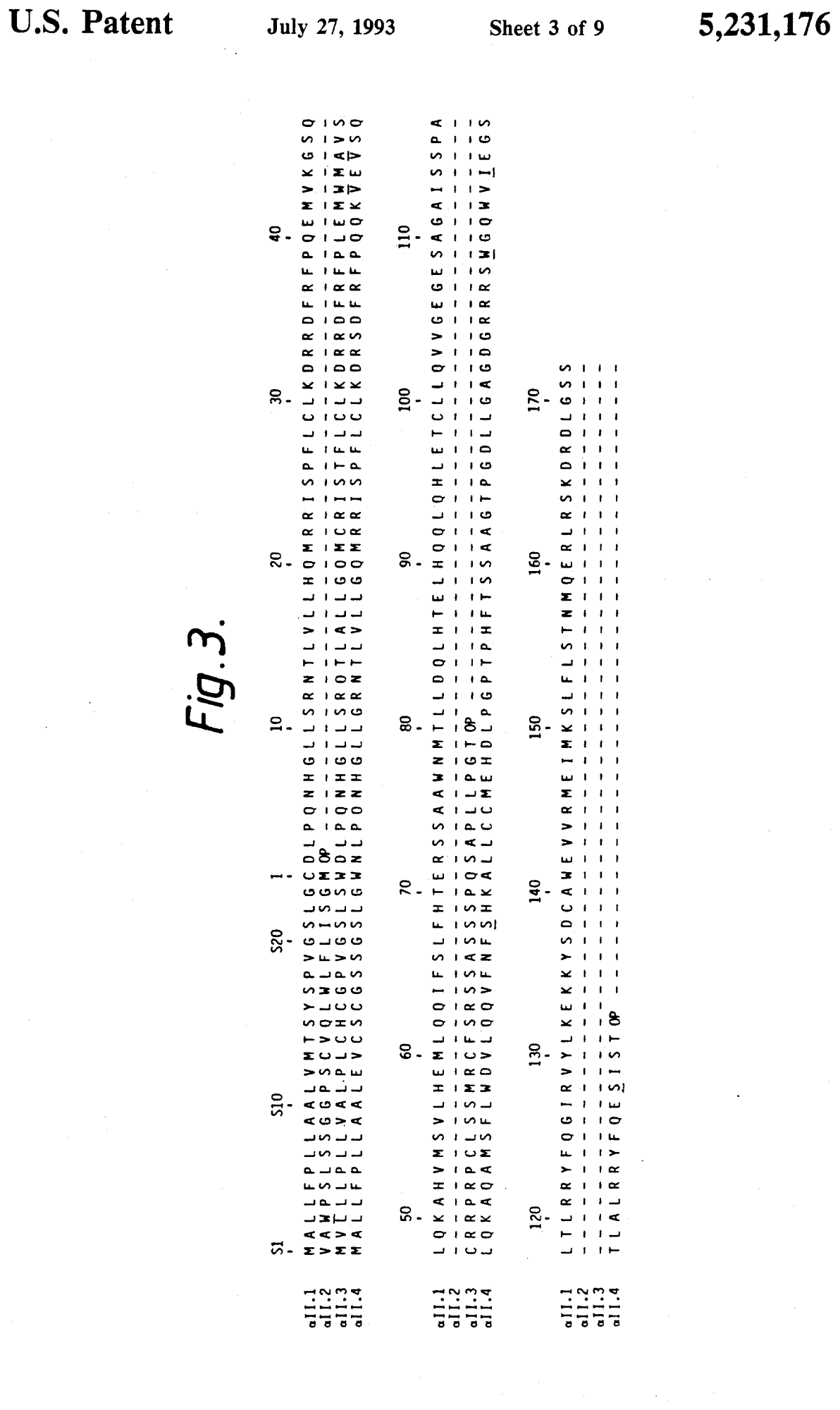

FIG. 3. Polypeptides encoded by the IFN-αII gene family. The complete amino acid sequence of the IFN-αII.1 preprotein is shown. The location of insertions/deletions within amino acid residues is indicated by underlining. The residues of the signal peptide of IFN-αII.1 are numbered S1–S23, and the residues of the mature protein are numbered 1–172.

FIGS. 6A–6C. Comparison of the nucleotide sequences of HuIFN-$α_{II}$1 with HuIFN-$α_I$1 and the proteins encoded by HuIFN-$α_{II}$1 with the members of the class I HuIFN-$α_I$1 gene family. Amino acid residues in HuIFN-$α_I$1 which are underlined represent those found in all of the class I HuIFN-α species reported to date. Amino acid residues below the HuIFN-$α_{II}$1 DNA sequence indicate differences between HuIFN-$α_{II}$1 and HuIFN-$α_I$1. Asterisks mark changes in the nucleotide sequence which do not result in a change in the amino acid encoded. The polyadenylation signal (AATAAA) of HuIFN-$α_I$1 is overlined. The proposed polyadenylation signal (ATTAAA) of HuIFN-$α_{II}$1 is underlined. The vertical arrow indicates the messenger RNA cap site of HuIFN-$α_I$1. The open triangles indicate the 5' end and 3' site of poly(A) addition found for the longest HuIFN-$α_I$1 cDNA clone.

FIG. 11). The 0.9 kb pLeIF A25 fragment contains the IFN-$α_I$2 coding region, and the 1.2 kb pHuIFN-$α_{II}$trp1 fragment contains the IFN-$α_{II}$1 coding region.

DETAILED DESCRIPTION: EXAMPLES

Identification of a human IFN-α gene (HuIFN-αII) Gene

A human genomic DNA library (11) was screened at low hybridization stringency utilizing a probe prepared from a fragment spanning the mature coding region of the HuIFN-β gene. Of seven positive clones recovered by this screening procedure, four proved to contain the HuIFN-β gene by restriction mapping, Southern analysis and hybridization at high stringency using the HuIFN-β probe. The remaining three recombinants appeared to represent overlapping segments of the human genome containing a distantly related gene which only hybridized to the HuIFN-β probe at low stringency. A 4.1 kilobase HindIII fragment containing the hybridizing region from one of these clones, λ24.1, was subcloned into pBR322 for further characterization by restriction endonuclease mapping (FIG. 4) and nucleotide sequencing.

DNA sequence analysis of this fragment (FIG. 6) reveals an interferon gene exhibiting substantially more nucleotide homology in its coding region with the HuIFN-α genes (for example, 70 percent with HuIFN-$α_I$1, Table 1) than with HuIFN-β (48 percent). Similarly, while the HuIFN-$α_I$1 protein and the gene product of λα24.1 each share only 30 percent amino acid homology with HuIFN-β, they are approximately 58 percent homologous with one another. It was concluded that the gene contained on λα24.1 encodes an IFN-α rather than an IFN-β. The sequence of this protein, however, is surprisingly dissimilar to the other HuIFN-α gene products.

Figure 6A:
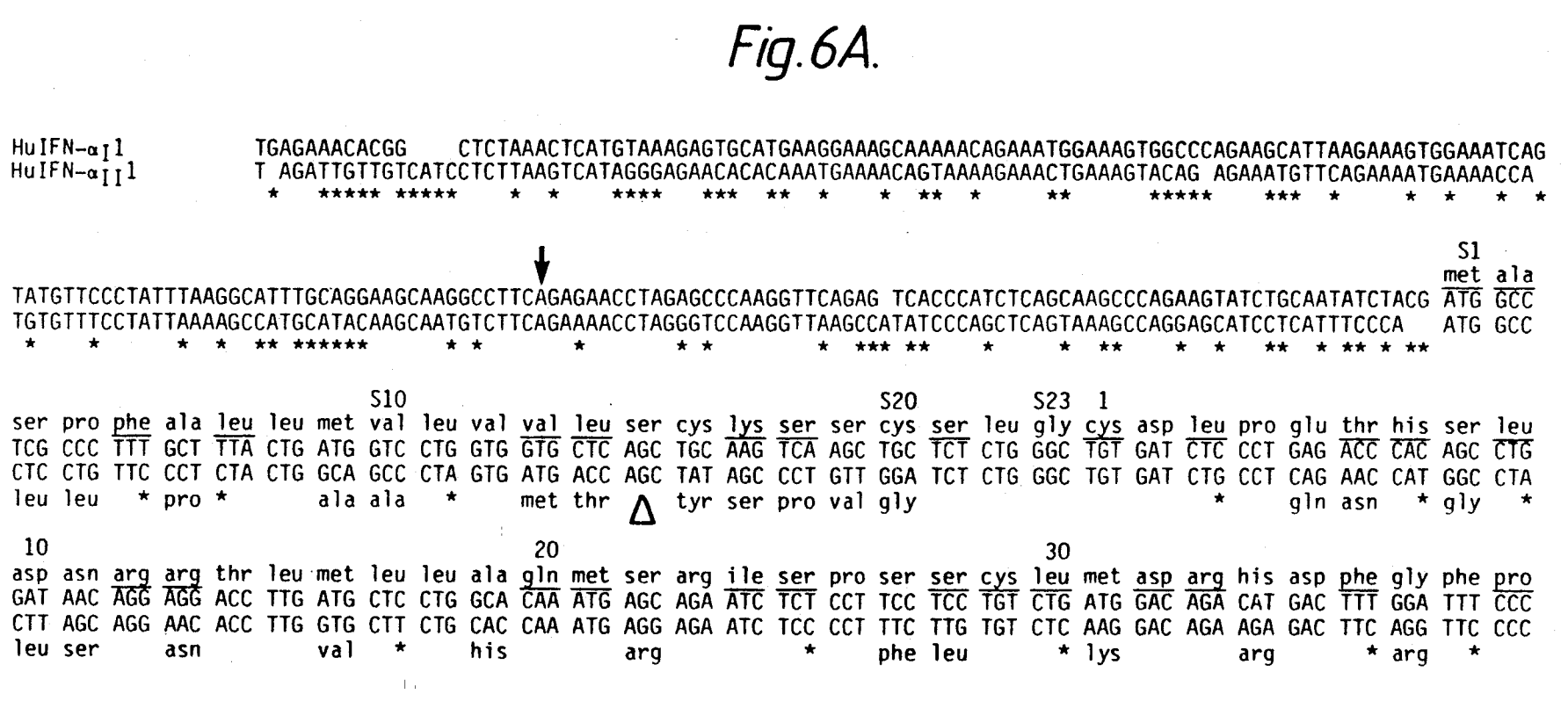
Figure 6B:
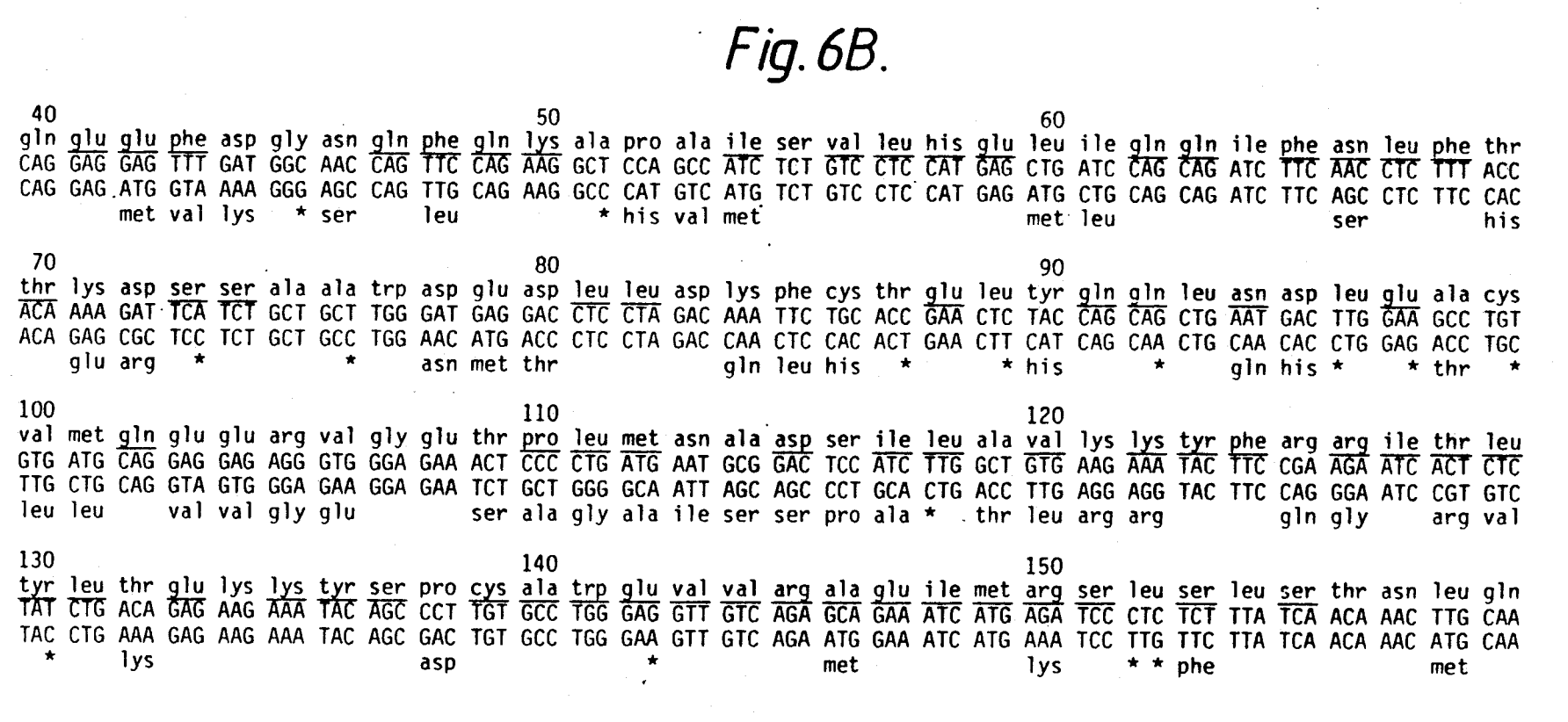
Figure 6C:
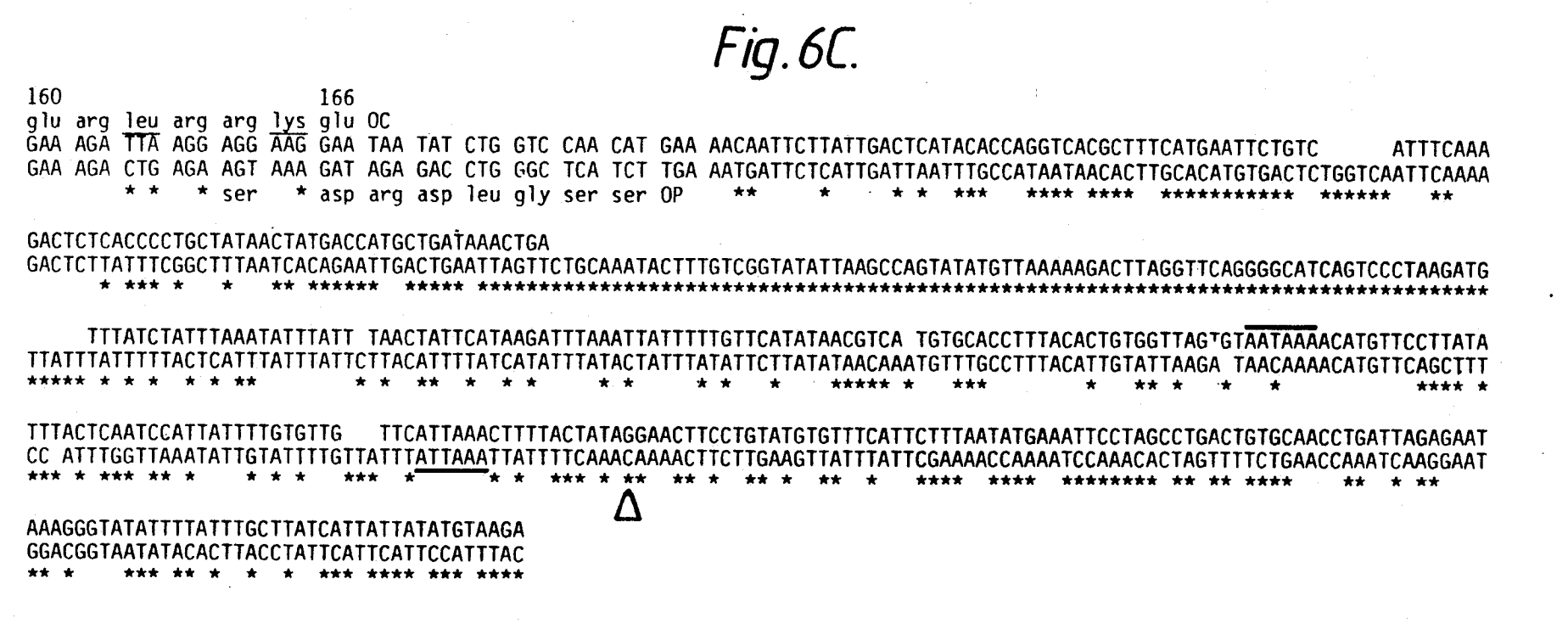

The novel HuIFN-α contains five or six additional amino acids at its carboxy terminus, three of which are identical in each protein (FIG. 6). These similarities are reflected at the level of nucleotide homology as well (Table 1). Taken together, these observations strongly suggest that this novel HuIFN-α represents a homologous gene product, distinct from the class I IFN-α gene family which includes the previously sequenced functional HuIFN-α genes. Accordingly, we have named this gene HuIFN-$α_{II}$1 to distinguish it from the class I HuIFN-α genes.

The HuIFN-$α_{II}$1 sequence contains a potential glycosylation sequence, asn-met-thr, at positions 78–80. Interestingly, a similar sequence is found at the same position in HuIFN-β which is known to be modified in vivo by carbohydrate addition (20).

Figure 5:
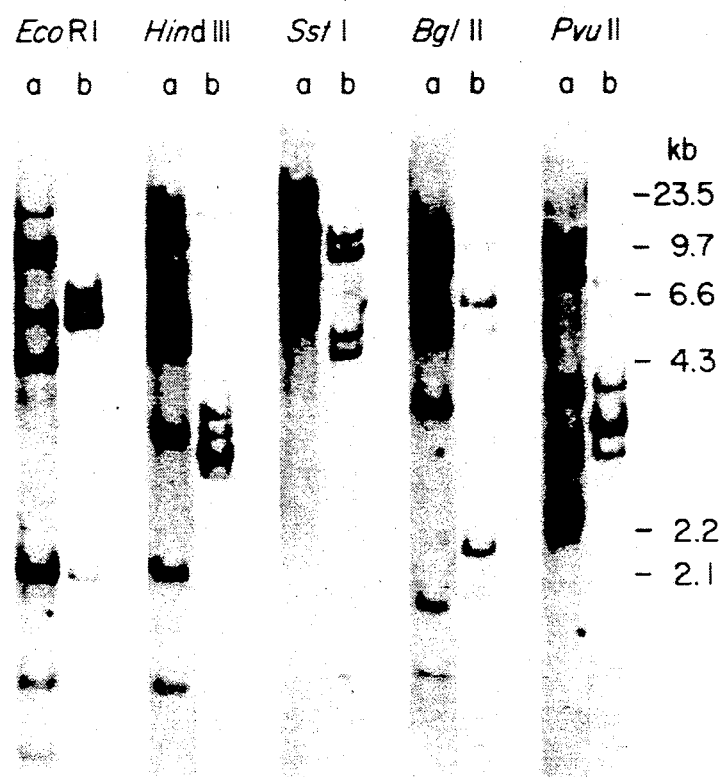
FIG. 5. Southern blot analysis of human IFN-α gene families. High molecular weight human genomic DNAs (5 μg) were digested with restriction endonucleases as shown, electrophoresed through a 0.8 percent agarose gel and subsequently transferred to nitrocellulose filter paper. Hybridizations were performed under stringent conditions using probes derived from the following IFN-α coding regions, HuIFN-$α_I$1 (lane a) and HuIFN-$α_{II}$1 (lane b). Molecular size standards correspond to EcoRI-digested bacteriophage λ Charon 30A and pBR322 DNAs and RsaI-digested pBR322 DNA.

To examine the possibility that HuIFN-$α_{II}$1 might define a new family of IFN-α genes in the human genome, blot-hybridization analysis was performed with human genomic DNA utilizing probes derived from the HuIFN-$α_I$1 and HuIFN-$α_{II}$1 coding region under stringent conditions which do not permit cross-hybridization of the two genes. The results of such an experiment, shown in FIG. 5, indicate that the HuIFN-$\alpha_I$1 and HuIFN-$\alpha_{II}$1 probes define distinct gene families. The HuIFN-$\alpha_{II}$1 probe demonstrates the presence of 6-7 class II genes in the human genome.

Expression of Class IFN-$\alpha$ Genes is Inducible by Virus

Figure 7A:
FIGS. 7A and 7B. Analysis of virally induced class I and class II IFN-α transcripts. Five microgram aliquots of polyA(+) RNA were analyzed in each lane. In (A) is shown hybridization with the class I (IFN-$α_I$2) probe and (B), hybridization with the class II (IFN-$α_{II}$1) probe. Lanes 1, 2, and 3 are samples from donor 1, lanes 4, 5, and 6 are samples from donor 2. Lanes 1 and 4 are uninduced controls. Lanes 2 and 5: induction by Newcastle Disease virus; lanes 3 and 6: induction with Sendai virus. The molecular size markers are derived from an EcoRI+PstI digestion of pLeIF A25 (3.6 kb and 0.9 kb) and an EcoRI+HindIII digestion of pHuIFN-$α_{II}$trp (4.3 kb and 1.2 kb.
Figure 7B:

The HuIFN-$\alpha_{II}$1 protein or related class II IFN-$\alpha$ gene products have not been identified in interferon preparations from virally-induced cell lines (21, 22), nor have the corresponding DNA sequences been found in cDNA libraries prepared from lymphoblastoid cell lines (3) or peripheral blood lymphocytes induced by viruses. To determine whether class II HuIFN-$\alpha$ genes are transcribed in response to virus infection, RNA from the peripheral blood lymphocytes of two donors induced with either Sendai or Newcastle Disease virus was analyzed by blot hybridization. Following a six hour incubation with virus, polyA+ RNA was isolated from the cultures, electrophoresed on formaldehyde gels, transferred to nitrocellulose filters and hybridized with either a class I (HuIFN-$\alpha_I$2) or class II (HuIFN-$\alpha_{II}$1) probe. As seen in FIG. 7, transcription of both the class I (FIG. 7A) and class II (FIG. 7B) IFN-$\alpha$ genes is induced by both Newcastle Disease virus (lanes 2 and 5) and Sendai virus (lanes 3 and 6), and is not detectable in uninduced cultures from either donor (lanes 1 and 4). To compare the levels of expression of the class I and class II genes, filters hybridized with each probe were exposed to film until DNA markers containing the coding regions of either HuIFN-$\alpha_I$2 (FIG. 7A) or HuIFN-$\alpha_{II}$1 (FIG. 7B) gave signals of equal intensity (data not shown). From this analysis it appears that the class II genes are transcribed at a level comparable to the class I genes (FIG. 7). In addition, it appears that Sendai virus induces several-fold more class I and class II interferon message than NDV. This suggests that the class I and class II genes are regulated similarly in response to viral infection.

To confirm the conclusion that the IFN-$\alpha_{II}$1 gene is expressed, a complementary DNA library was constructed from polyA(+) RNA isolated from Sendai-induced peripheral blood lymphocytes. A HuIFN-$\alpha_{II}$1 coding region probe was employed to screen 10,000 plaques under stringent hybridization conditions. Two HuIFN-$\alpha_{II}$1 clones were recovered. DNA sequence analysis showed that the longer of the two cDNA clones extended from the poly(A) of the mRNA to within the sequence encoding the signal peptide of HuIFN-$\alpha_{II}$1. The corresponding sequence within the HuIFN-$\alpha_{II}$1 gene is indicated in FIG. 6.

Class II IFN-$\alpha$ Genes Encode Proteins with Antiviral Activity

To determine whether class II IFN-$\alpha$ genes encode active proteins and to compare their host range with those of class I IFN-$\alpha$ polypeptides, bacterial vectors were constructed for the expression of HuIFN-$\alpha_{II}$1 genes. The resulting plasmids join a trp operon promoter, ribosome-binding site and initiator methionine codon to the first amino acid residue of each mature IFN-$\alpha$ coding region. As shown in Table 2, extracts prepared from E. coli strains transformed with each of the three plasmids and grown under conditions leading to depletion of tryptophan from the growth media contain significant amounts of antiviral activity as measured by cytopathic effect inhibition assays. The relative activities of each IFN-$\alpha$ were compared with those of two class I HuIFN-$\alpha$ proteins, HuIFN-$\alpha_I$2 and HuIFN-$\alpha_I$1, on a bovine cell line (MDBK) cell line challenged with vesicular stomatitis virus and on a human lung carcinoma (A549) cell line challenged with encephalomyocarditis virus. HuIFN-$\alpha_{II}$1 and HuIFN-$\alpha_I$2, show approximately equal activity on each cell type. The class II IFN-$\alpha$ proteins therefore appear to have specificities which overlap those of several class I IFN-$\alpha$ gene products in these as well as other cell lines.

To further characterize the antiviral activity associated with HuIFN-$\alpha_{II}$1, we examined the ability of antisera prepared against IFN-$\alpha$ and IFN-$\beta$ to neutralize HuIFN-$\alpha_{II}$1 activity. Anti-HuIFN-$\beta$ did not significantly affect the activity of HuIFN-$\alpha_{II}$1, while an antisera prepared against Sendai-virus induced interferon from human leukocyte cultures did neutralize HuIFN-$\alpha_{II}$1 antiviral activity (Table 3). Since the latter induction protocol has been shown to result primarily in the production of HuIFN-$\alpha$ rather than HuIFN-$\beta$, these results confirm the assignment of HuIFN-$\alpha_{II}$1 to the IFN-$\alpha$ family, made on the basis of protein homology.

Two Distinct IFN-$\alpha$ Gene Families

Previous studies have described a family of approximately fifteen non-allelic human IFN-$\alpha$ genes, which are related by at least 85 percent nucleotide homology in their coding regions (3). For clarity, these genes are referred to as the HuIFN-$\alpha_I$ family. Each gene encodes a functional interferon polypeptide as determined by its ability to program the expression of antiviral activity in E. coli.

Such a gene was identified, HuIFN-$\alpha_{II}$1, among a collection of clones initially isolated by screening a human genomic library with a HuIFN-$\beta$ cDNA probe. Comparison of DNA homologies, however, as well as antigenicity studies on the HuIFN-$\alpha_{II}$1 protein expressed in E. coli, firmly establish that this gene encodes an IFN-$\alpha$ rather than an IFN-$\beta$ protein. HuIFN-$\alpha_{II}$1 encodes a mature polypeptide of 172 amino acid residues. These results demonstrate the existence of two homologous, but distinct IFN-$\alpha$ gene families in the human genome.

Southern blot analysis of human DNA suggests that the class II HuIFN-$\alpha$ gene family may contain as many as 6-7 different members.

The members of the class I HuIFN-$\alpha$ family, as well as HuIFN-$\beta$, have been localized to chromosome 9, (23), while the gene for HuIFN-$\gamma$ is found on chromosome 12 (24). Recent experiments indicate that most, if not all, members of the class II HuIFN-$\alpha$ family are also located on chromosome 9.

Transcriptional Control of Class II IFN-$\alpha$ Genes

Differential regulation of IFN-$\alpha$ mRNA levels has been suggested by the greater than ten-fold range in frequency with which individual HuIFN-$\alpha$ mRNA sequences are found in virally-induced cell cultures. In our efforts to compare transcriptional regulation of class I and II IFN-$\alpha$ genes, we have employed Newcastle Disease virus (NDV) or Sendai virus to induce interferon synthesis in human peripheral blood lymphocytes. Comparable levels of class I and class II mRNA were readily observed in polyA(+)-RNA prepared from each culture following six hours of viral induction (FIG. 7). In addition, Sendai virus appeared to induce several-fold more IFN-$\alpha$ transcripts of class II, as well as class I types, indicating similar transcriptional activation of either IFN-$\alpha$ family by viral induction. In light of the observation that class II cDNA clones were not represented among libraries prepared from Sendai virus-induced cultures of human leukocytes or a human myeloblastoid cell line, this is the first evidence for the viral induction of class II IFN-α synthesis. This result has been further confirmed by the isolation of a complementary DNA clone which includes the 3'-end of the IFN-$\alpha_{II}1$ mRNA, and most of its coding region (FIG. 6).

Hybridization Conditions and Probes

Figure 8:
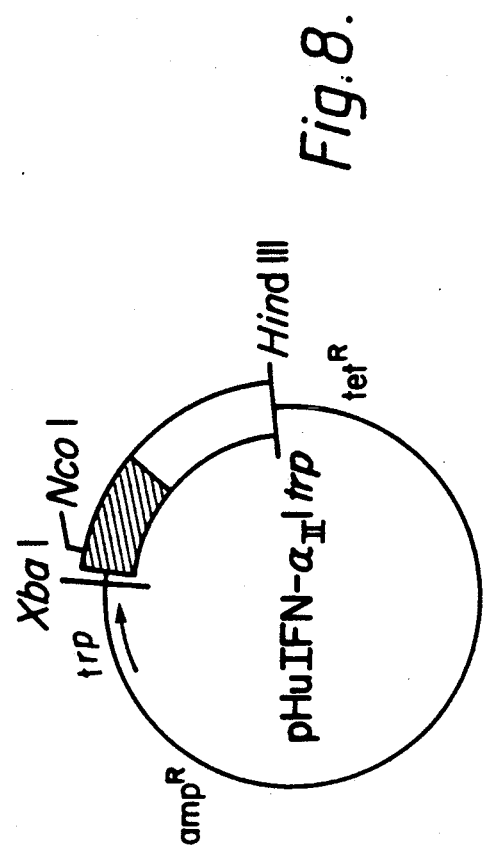
FIG. 8. Structure of plasmid directing the synthesis of mature IFN-α proteins in *E. coli*. The thick segment represents the IFN-α insert, with the mature coding region shaded: HuIFN-$α_{II}$1trp.

Hybridizations were performed in 5XSSC (1XSSC is 0.15M NaCl, 0.015M sodium citrate), 5X Denhardt's solution (12), 0.1 percent sodium dodecyl sulfate (SDS), 0.1 percent sodium pyrophosphate, 50 μg/ml sonicated, denatured salmon sperm DNA and 10 percent sodium dextran sulfate, containing either 20 percent or 50 percent formamide for non-stringent and stringent conditions, respectively. After incubation at 42° C., filters were washed at room temperature in 2XSSC, 0.2 percent SDS (non-stringent) or 42° C. in 0.2XSSC, 0.1 percent SDS (stringent). $^{32}$P-labeled probes were prepared as described by (13). For the analysis of class I and II genes in human DNA at high stringency (FIG. 5), the following fragment was employed (each contained the mature coding region of the corresponding IFN-α gene): class I human, the 565 bp EcoRI fragment of pHuIFN-$\alpha_{I}2/1$ BglII hybrid (14); class II human, the 390 bp XbaI-AccI fragment of pHuIFN-$\alpha_{II}1$ (see FIG. 8 for description of plasmids).

Construction and Screening of Phage Libraries

The HuIFN-$\alpha_{II}1$ gene was isolated from a human fetal liver/bacteriophage λ Charon 4A library constructed by Lawn et al. (11) utilizing a probe prepared from the 501 bp XbaI-BglII fragment encoding the mature HuIFN-β protein.

double-stranded cDNA was ligated into the λgt10 vector (25).

Construction of Bacterial Expression Plasmids for IFN-α Genes:

The construction of plasmids placing the expression of h mature HuIFN-$\alpha_{I}1$ and -$\alpha_{I}2$ under the control of the E. coli trp promoter have been previously described (2, 14). Similar constructions were made which place the N-terminal amino acid residue of mature HuIFN-$\alpha_{II}1$ directly adjacent to an initiator methionine codon, ribosome binding site and trp promoter, as follows: A synthetic DNA duplex containing an XbaI cohesive end, an ATG codon, the codons for amino acids 1-7 of the mature protein, and ending with an NcoI cohesive terminus was joined to 1290 bp NcoI-HindIII fragment containing the remainder of the HuIFN-$\alpha_{II}1$ coding sequences, and inserted into a trp expression vector, pHGH207-1 (20), between the XbaI and HindIII sites of this plasmid.

Detection of IFN-α Antiviral Activity in E. coli

Overnight cultures of E. coli K12 strain 294 transformed with the appropriate expression plasmids were grown, harvested and extracted for antiviral assay (15). Interferon activity was determined by cytopathic effect (CPE) inhibition assays using either bovine kidney cells (MDBK) or human lung carcinoma cells (A549) obtained from the American Type Culture Collection, Rockville, Md. Vesicular stomatitis (VS) and encephalomyocarditis (EMC) viruses were grown and used in the CPE inhibition assays (14). Values determined by this method are expressed as units relative to the NIH leukocyte standard G-023-901-527.

The antigenic identity of HuIFN-$\alpha_{II}1$ was determined by (14).

TABLE 1

| Pairwise comparison of homology in coding regions of Human IFN-α genes. | | | |
|---|---|---|---|
| | HuIFN-αI.1 | HuIFN-αII.1 | |
| HuIFN-αI.1 | | 70.0 | Percent Nucleotide Homology |
| HuIFN-αII.1 | 57.7 | | |
| | Percent Amino Acid Homology | | |

Shown are the percent amino acid sequence homologies between pairs of interferon preproteins (lower left) and the percent nucleotide homology between the corresponding coding regions (upper right). The six additional C-terminal amino acid residues, or 18 added nucleotides, of the class II interferons (FIGS. 5 and 7) are not included in comparisons with the class I interferons.

DNA Sequence Analysis

DNA sequences were determined as described by (16) or by subcloning DNA fragments into M13 mp8 and mp9 vectors (17) and employing the dideoxy chain termination method (18).

Preparation and Analysis of Virally Induced RNA

Peripheral blood lymphocytes ($2 \times 10^9$) were resuspended at $4 \times 10^6$ cells per ml in RPMI 1640 containing 5 percent (heat inactivated) fetal calf serum. Cultures were incubated in T-175 flasks (Falcon) and induced cultures were treated with 25 UAU/$10^6$ cells of Newcastle Disease virus or Sendai virus. Following six hours of incubation with virus, the cultures were treated with 0.05 percent EDTA and cells were harvested by centrifugation, washed once with ice-cold medium, and polyA(+) RNA was prepared (19). Formaldehyde gel electrophoresis of RNA and Northern blot analysis were carried out. The peripheral blood lymphocyte cDNA library was constructed (2) except that

TABLE 2

| IFN-α Activity in Extracts of E. coli | | | |
|---|---|---|---|
| E. coli 294 transformed by: | IFN-α activity (units/liter culture) | | Ratio A549/MDBK |
| | A549-EMC | MDBK-VSV | |
| pHuIFN-$\alpha_{I}1$ | $2.5 \times 10^5$ | $1.9 \times 10^6$ | 0.13 |
| pHuIFN-$\alpha_{I}2$ | $1.4 \times 10^8$ | $1.3 \times 10^8$ | 1.1 |
| pHuIFN-$\alpha_{II}1$ | $5.0 \times 10^5$ | $4.7 \times 10^5$ | 1.1 |

Interferon antiviral activities on human and bovine cells. E. coli K12 (strain 294) cultures containing the appropriate expression plasmids were grown and lysates were prepared for interferon bioassay. Interferon antiviral activity in the lysates was determined in a cytopathic effect inhibition assay employing MDBK (bovine kidney) cells and vesicular stomatitis virus or A549 (human lung carcinoma) cells challenged with encephalomyocarditis virus. Results are expressed as the amount of antiviral activity per liter of bacterial culture grown to an optical density of 1.0 at 550 nM.

TABLE 3

| HuIFN-$\alpha_{II}1$ Activity is Neutralized by Antibody to HuIFN-α | | | |
|---|---|---|---|
| | Interferon Activity (units/ml) | | |
| Interferon | Control | +AntiIFN-α | +AntiIFN-β |
| HuIFN-$\alpha_{I}2$ | 64 | <4 (>16) | 32 (2) |

TABLE 3-continued

HuIFN-$\alpha_{II}$1 Activity is Neutralized by Antibody to HuIFN-$\alpha$

| Interferon | Interferon Activity (units/ml) | | |
|---|---|---|---|
| | Control | +AntiIFN-$\alpha$ | +AntiIFN-$\beta$ |
| HuIFN-$\alpha_{II}$1 | 384 | <4 (>96) | 192 (2) |
| Natural HuIFN-$\alpha$ | 128 | <4 (>32) | ND |
| Natural HuIFN-$\beta$ | 64 | ND | <4 (>16) |

Interferon was prepared and assayed as in the legend to Table 2. AntiIFN-$\alpha$ was prepared by immunization of a rabbit with natural HuIFN-$\alpha$ purified. AntiIFN-$\beta$ was prepared by immunization of a calf with natural HuIFN-$\beta$ purified. Numbers in parentheses give the fold reduction in antiviral activity following treatment with antisera.

TABLE 4

Percentage Corrected Nucleotide Divergence of Class I and II IFN-$\alpha$ Coding Regions

| | Replacement Sites (Percent) | Silent Sites (Percent) |
|---|---|---|
| HuIFN-$\alpha_I$1/HuIFN-$\alpha_{II}$1 | 30.27 | 69.19 |

Figure 1:
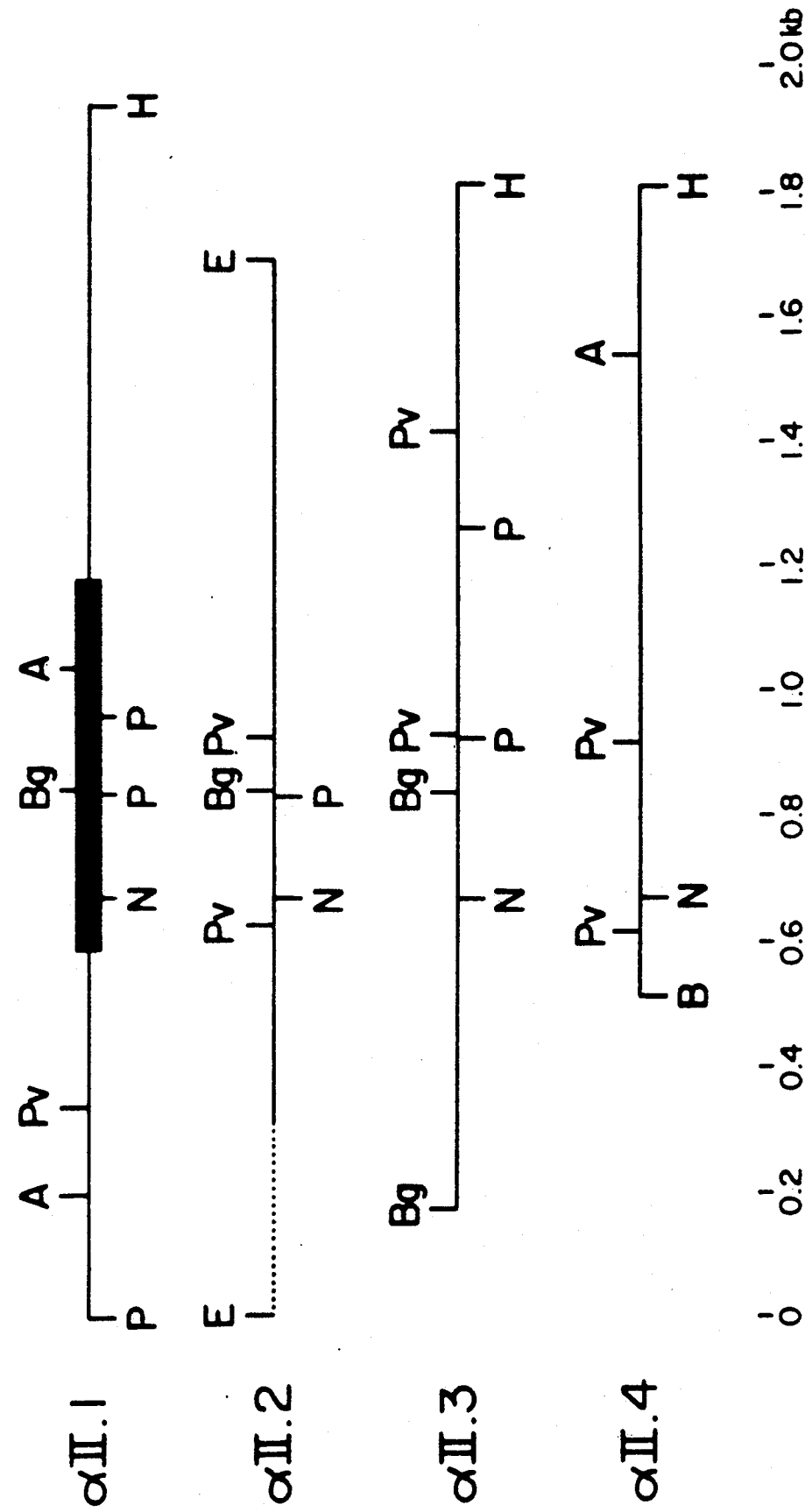
FIG. 1. Alignment of IFN-αII genes by restriction endonuclease mapping. Restriction endonuclease sites included in the sequenced regions of the genes (FIG. 2) are shown, except for the region between 0.0 kb and 0.3 kb of the IFN-αII.2 gene. The thickened portion of the map of IFN-αII.1 corresponds to the sequence encoding the IFN preprotein. A size scale in kilobase pairs (kb) is shown below the maps. Restriction endonuclease sites within the IFN-αII genes are indicated as follows: Acc1 (A), BamHI (B), BglII (Bg), EcoRI (E), HindIII (H), Nco1 (N), PstI (P), PvuII (Pv).
Figure 2A:
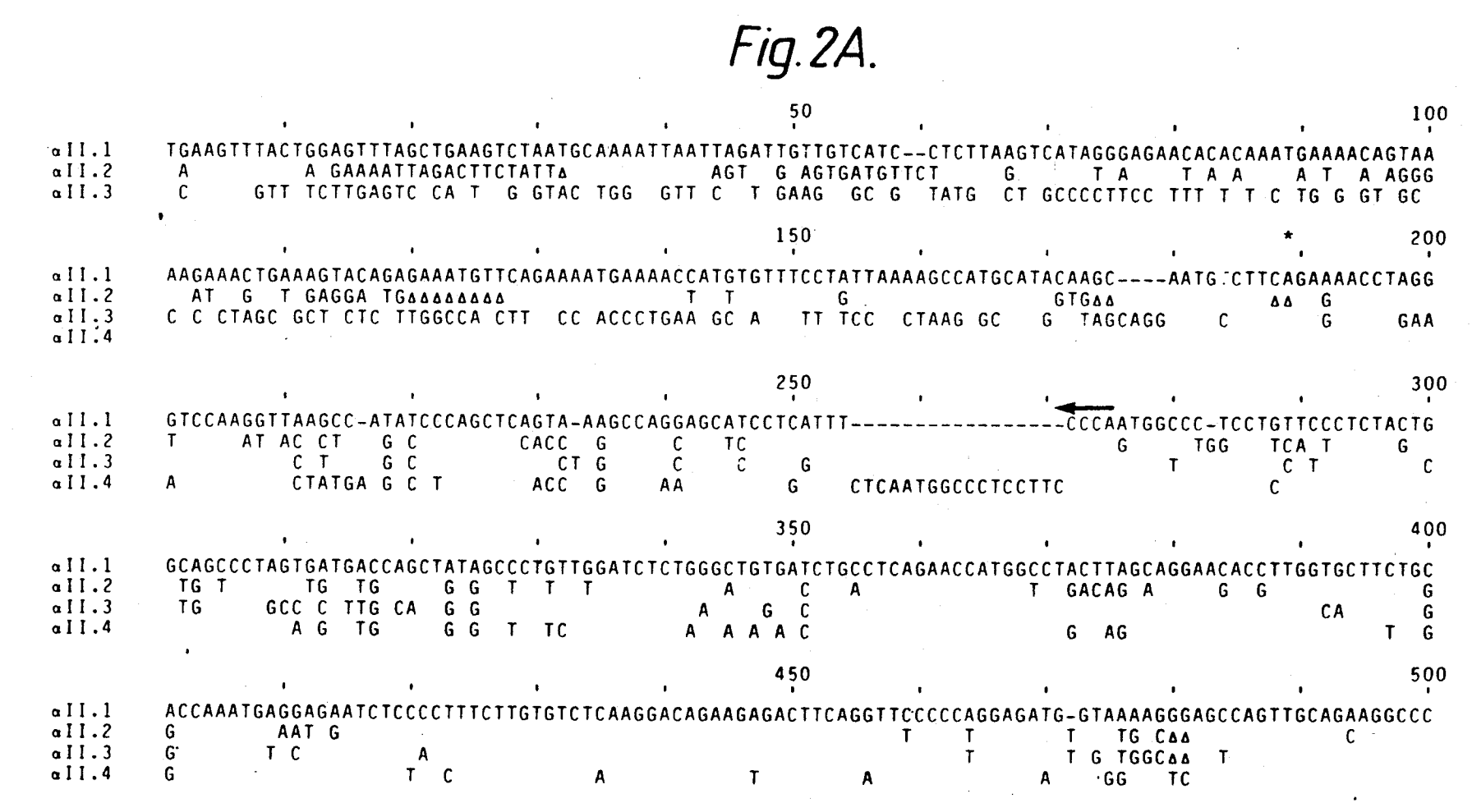
Figure 4:
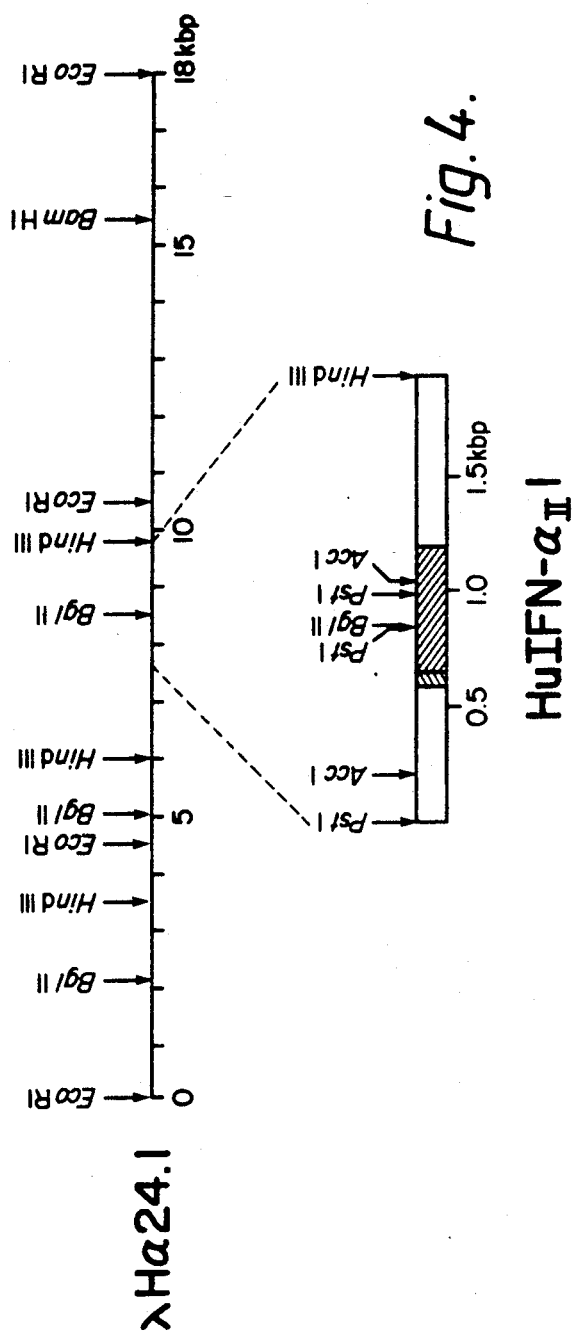
FIG. 4. The structures of phage recombinants containing the HuIFN-$α_{II}$1 genes. The coding region is shown cross-hatched, and is divided into the presequence (hatched left) and the restriction map of the HuIFN-$α_{II}$1 gene and flanking regions from the recombinant phage λ24.1 is shown.

The percentage corrected divergence for each pair of nucleotide sequences were calculated. Nucleotide sequences were aligned as shown in FIGS. 2 and 4. The last 18 nucleotides of the class II IFN-$\alpha$ genes (encoding amino acids 167-172) were compared with one another, but were excluded in class I vs. class II comparisons.

The human leukocyte interferons of the present invention are characterized by having a probable broader spectrum of biological activity compared with previously reported human leukocyte interferons (see, for example, 4). The novel, distinct leukocyte interferons of the present invention are further characterized from those human leukocyte interferons previously reported by having less than about 70 percent (most usually in the range of about 50–60 percent) homology on the amino acid level with said previously reported human leukocyte interferons (4). Further, the novel, distinct human leukocyte interferons of the present invention are characterized by having more than 166 amino acid residues in their mature form, most preferably having about 172 amino acids in their mature form.

While specific embodiments are disclosed herein, it is understood that the present invention is not to be construed as limited to such, rather to the lawful scope of the appended claims.

BIBLIOGRAPHY

1. Isaacs et al., *J. Proc. R. Soc.* B147, 258 (1957).
2. Goeddel et al., *Nature* 287, 411 (1980).
3. Goeddel et al., *Nature* 290, 20 (1981).
4. European Patent Application Publication No. 0043980.
5. European Patent Application Publication No. 0032134.
6. European Patent Application Publication No. 0088622.
7. European Patent Application Publication No. 0048970.
8. Gray et al., *Nature* 295, 503 (1982).
9. European Patent Application Publication No. 0077670.
10. Rinderknecht et al., *J. Biol. Chem.* 259, 67 (1984).
11. Lawn, *Cell* 15, 1157 (1978).
12. Denhardt, *Biochem. Biophys. Res. Comm.* 23, 641 (1966).
13. Taylor et al., *Biochem. Biophys. Acta* 442, 324 (1976).
14. Weck et al., *Nucleic Acids Res.* 9, 6153 (1981).
15. Goeddel et al., *Nucleic Acids Res.* 8 4057 (1980).
16. Maxam, A. M. et al., *Meth. Enzymol.* 65, 499 (1980).
17. Messing et al., *Nucleic Acids Res.* 9, 309 (1981).
18. Sanger et al., *Proc. Natl. Acad. Sci.* (U.S.A.) 74, 5463 (1977).
19. Ullrich et al., *Science* 196, 1313 (1977).
20. Havell et al., *J. Biol. Chem.* 252, 4425 (1977).
21. Zoon et al., *Science* 207, 527 (1980).
22. Allen et al., *Nature* 287, 408 (1980).
23. Owerback et al., *Proc. Natl. Acad. Sci.* (U.S.A.) 78, 3123 (1981).
24. Naylor et al., *J. Exp. Med.* 57, 1020 (1983).
25. Huynh et al., *DNA Cloning Techniques: A Practical Approach*, Ed. D. Glover, IRL Press (1984).

We claim:

1. A purified DNA molecule encoding a human leukocyte interferon containing in its mature form greater than 166 and no more than 172 amino acids.

2. DNA molecule encoding human leukocyte interferon according to claim 1 having the sequence depicted by HuIFN-$\alpha$II.1 from position 1 through 172 as depicted in FIG. 6 hereof.

3. Expression vector suitable for transfection of a microorganism or cell culture, operably harboring DNA encoding human leukocyte interferon according to claim 1.

4. Expression vector of claim 3 operably harboring DNA molecule according to claim 2.

5. A microorganism or cell culture capable of producing human leukocyte interferon according to claim 1.

6. A microorganism or cell culture transfected with an operable expression vector harboring DNA as defined in claim 3.

7. A process which comprises producing by recombinant DNA expression human leukocyte interferon according to claim 1 in a microorganism or cell culture according to claim 6.

* * * * *